(12) United States Patent
Ouchi et al.

(10) Patent No.: US 6,911,005 B2
(45) Date of Patent: Jun. 28, 2005

(54) ENDOSCOPE WITH DETACHABLE SHEATH

(75) Inventors: Teruo Ouchi, Saitama-ken (JP); Kazuyuki Yamamoto, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/278,811

(22) Filed: Oct. 24, 2002

(65) Prior Publication Data

US 2003/0083548 A1 May 1, 2003

(30) Foreign Application Priority Data

| Oct. 25, 2001 | (JP) | 2001-327085 |
|---|---|---|
| Oct. 25, 2001 | (JP) | 2001-327086 |
| Oct. 30, 2001 | (JP) | 2001-332345 |

(51) Int. Cl.[7] ............................................. A61B 1/00
(52) U.S. Cl. ..................... 600/121; 600/124; 600/125
(58) Field of Search ................................ 600/121, 122, 600/123, 124, 125

(56) References Cited

U.S. PATENT DOCUMENTS

| 4,646,722 A | * | 3/1987 | Silverstein et al. | ......... 600/104 |
| 4,721,097 A | * | 1/1988 | D'Amelio | ................... 600/123 |
| 4,991,564 A | | 2/1991 | Takahashi et al. | |
| 4,991,565 A | | 2/1991 | Takahashi et al. | |
| 5,050,585 A | * | 9/1991 | Takahashi | ................... 600/123 |
| 5,105,800 A | | 4/1992 | Takahashi et al. | |
| 5,159,919 A | * | 11/1992 | Chikama | .................... 600/124 |
| 5,419,310 A | * | 5/1995 | Frassica et al. | ............. 600/121 |
| 5,681,262 A | * | 10/1997 | Isse | ............................. 600/127 |

FOREIGN PATENT DOCUMENTS

| JP | 3-29635 | 2/1991 |
| JP | 3-37029 | 2/1991 |
| JP | 3-37030 | 2/1991 |
| JP | 3-101903 | 10/1991 |
| JP | 3-101906 | 10/1991 |
| JP | 4-28332 | 1/1992 |
| JP | 4-357920 | 12/1992 |
| JP | 5-49592 | 3/1993 |
| JP | 6-58902 | 8/1994 |
| JP | 6-63003 | 9/1994 |
| JP | 7-155282 | 6/1995 |
| JP | 8-308784 | 11/1996 |

* cited by examiner

Primary Examiner—Beverly M. Flanagan
(74) Attorney, Agent, or Firm—Greenblum & Bernstein, P.L.C.

(57) ABSTRACT

Combination of an endoscope and a sheath for covering an inserting tube of the endoscope, the sheath includes an elastic tubular member having an open proximal end and a closed distal end, and the endoscope is provided with an air feeding tube for feeding air from a distal end of the inserting tube to inflate the tubular member when the inserting tube is inserted into the tubular member to be covered therewith.

7 Claims, 9 Drawing Sheets

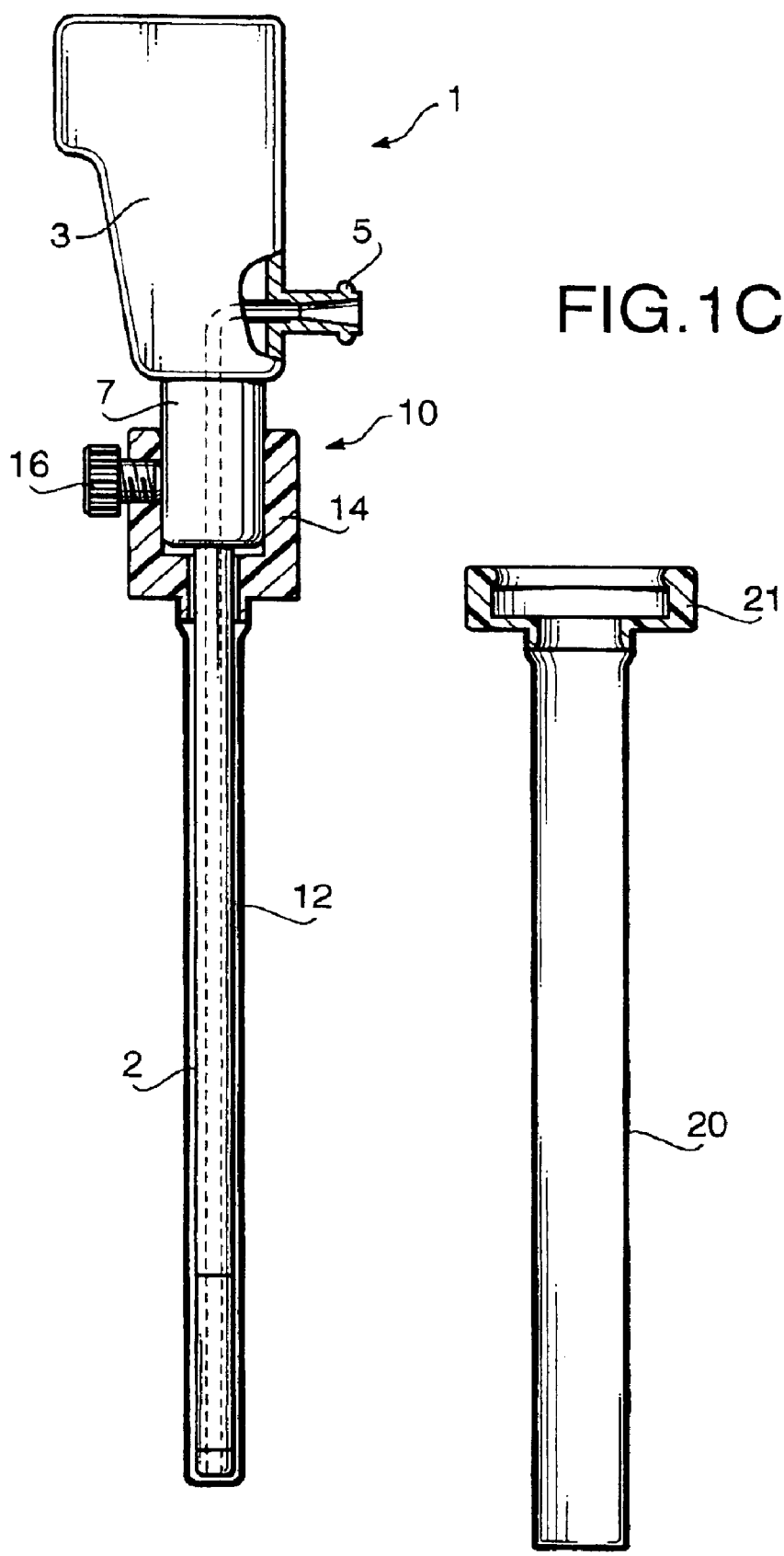

ENDOSCOPE WITH DETACHABLE SHEATH

BACKGROUND OF THE INVENTION

The present invention relates to an endoscope and a sheath which detachably covers an inserting tube of the endoscope.

Conventionally, the inserting tube of an endoscope is covered with a detachable sheath that is exchanged and discarded after each endoscopic inspection in order to prevent infection between patients via the endoscope.

The sheath includes an elastic tubular portion for covering the inserting tube and a cylindrical supporting portion connected to the proximal end of the tubular portion so as to allow the inserting tube to be inserted into the tubular portion through the supporting portion. The supporting portion is provided with an air feeding conduit for feeding air into and thereby inflating the tubular portion, and a packing for sealing a gap around the inserting tube being passed therethrough to prevent leaking of the air fed into the tubular portion.

The tubular portion is formed to have an inner diameter smaller than the outer diameter of the inserting tube. When inserting the inserting tube into the tubular portion in order to be covered therewith, the tubular portion is inflated by feeding air into it. The air feeding is stopped after the inserting tube has been fully inserted into the sheath so that the tubular portion shrinks and adheres on the inserting tube. In this manner, the inserting tube is covered with the tubular portion of the sheath without having any portion where the tubular portion floats therefrom. The sheath is put on the inserting tube in a manner as above since a floating portion of the sheath may cause the sheath to be snagged and even torn on a body wall when the inserting tube is inserted into a human body.

The conventional sheath, however, is relatively expensive since it is provided with the packing and the conduit for air feeding. Thus, the sheath has been one of the causes of increasing the endoscopic inspection cost.

SUMMARY OF THE INVENTION

The present invention is advantageous in that it provides an endoscope with a detachable sheath in which the sheath has a simple arrangement and can be produced at low-cost.

According to an aspect of the invention, there is provided a combination of an endoscope and a sheath for covering an inserting tube of the endoscope. The sheath includes an elastic tubular member which has an open proximal end and a closed distal end and has an inner diameter smaller than an outer diameter of the inserting tube. The endoscope is provided with an air feeding tube for feeding air from a distal end of the inserting tube to inflate the tubular member when the inserting tube is inserted into the tubular member to be covered therewith.

By the endoscope arranged as above, the sheath can be produced at low-cost since the air for inflating the sheath is fed by the air feeding tube of the endoscope and therefore it is not necessary to form a conduit to the sheath for feeding air into the sheath.

Optionally, the air feeding tube is arranged to be connectable with an external air supplying device at an operation portion of the endoscope. For example, a nipple is provided to the operation portion, which is connectable with an air supply tube of the external air supplying device, and the air feeding tube arranged so as to be in communication with the nipple.

Optionally, the open proximal end of the tubular member is connected to a cylindrical mounting member which is fixable to the endoscope to keep the tubular member from coming off from the inserting tube. At least a part of the mounting member is formed so as to allow the inserting tube to pass therethrough with a gap therebetween for discharging air fed into the tubular member through the air feeding tube. The gap serves to prevent bursting of the inflated tubular member.

According to another aspect of the invention, the sheath includes an elastic tubular member having an inner diameter larger than an outer diameter of said inserting tube, and the tubular member detachably covers the inserting tube by receiving said inserting tube thereinto and being stretched therealong to reduce the inner diameter so as to tightly contact said inserting tube.

The sheath arranged as above does not need to be inflated for covering the inserting tube since it has a larger inner diameter than the outer diameter of the inserting tube and hence it is not necessary to provide to the sheath a conduit for feeding air into the sheath. Accordingly, the sheath can be produced at low-cost.

Optionally, the tubular member has a length shorter than the inserting tube and is stretched so as to cover the inserting tube along the entire length thereof.

Optionally, the sheath includes a mounting member connected to a proximal end of the tubular member. The mounting member is provided with a manually operatable screw and is fixable to the endoscope at an engaging portion provided at a proximal end of the inserting tube by the screw to keep the sheath from coming off from the inserting tube. Further optionally, the engaging portion has a groove on an outer surface thereof which is formed to receive a tip end of the screw and thereby keep the mounting member fixed threreto.

Optionally, the endoscope includes an air suction tube for sucking air remaining between the inserting tube and the tubular member covering said inserting tube. In some embodiments of the invention, the air suction tube extends through the inserting tube and an operation portion of the endoscope from an opening formed at a distal end of the inserting tube to a nipple which is provided to the operation portion and adapted to be connected to an external device, such as a syringe, for sucking air.

Optionally, the nipple is provided with a cock to open/close the nipple.

Alternatively, the nipple includes a movable member and a biasing member. The movable member is arranged so as to be biased by the external device to a first position to open the nipple when the external device is connected to the nipple. The movable member is also arranged so as to be biased by the biasing member to a second position to close the nipple when the external device is disconnected from the nipple.

BRIEF DESCRIPTION OF THE ACCOMPANYING DRAWINGS

FIGS. 1A through 1C show an endoscope with a detachable sheath and a sheath cover according to a first embodiment of the invention;

FIG. 2 schematically shows an inserting tube of the endoscope shown in FIG. 1A being partially inserted into an elastic tubular member of the sheath also shown in FIG. 1A.;

DETAILED DESCRIPTION OF THE EMBODIMENTS

Figure 1A:
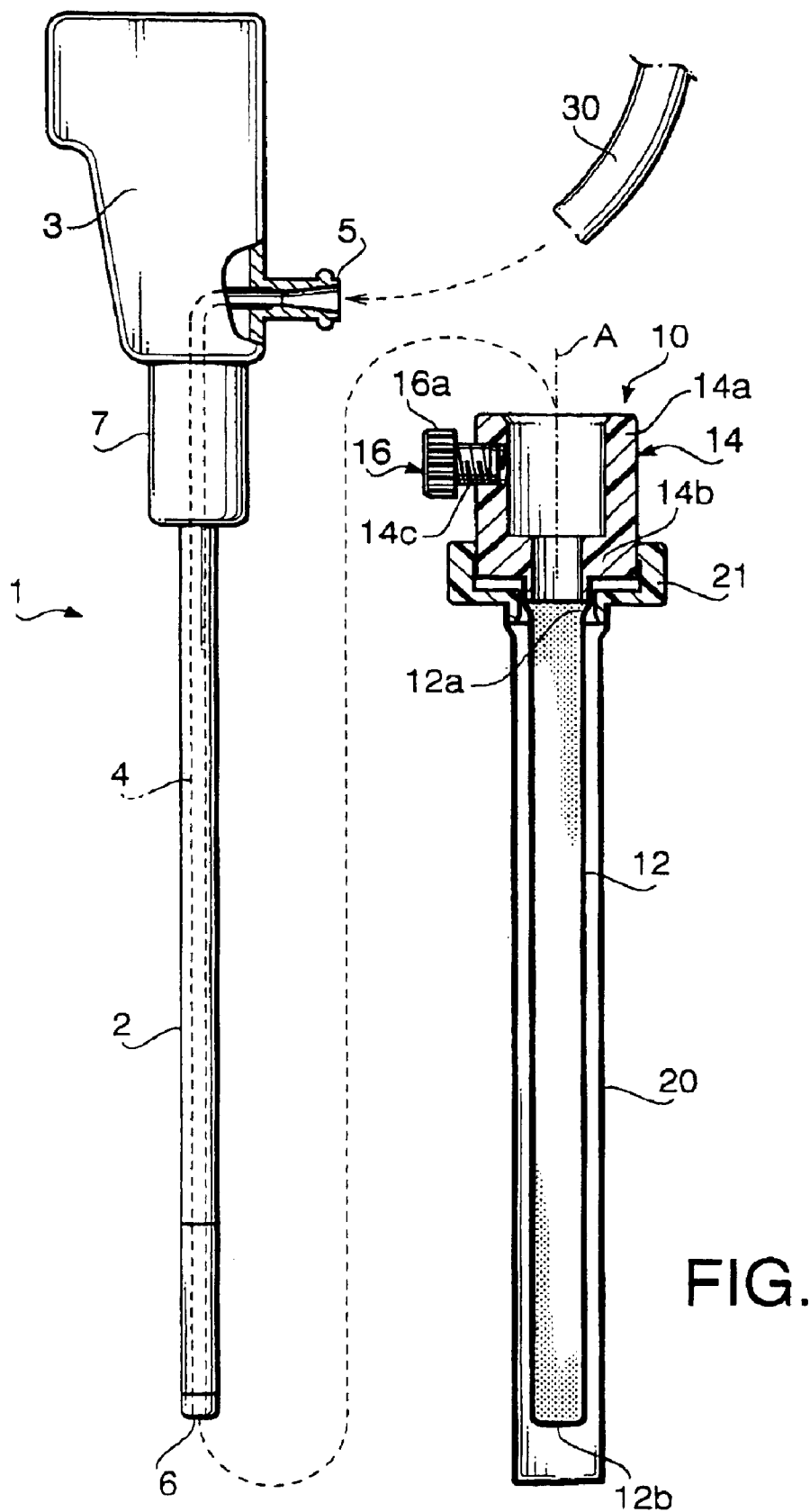

Hereinafter, embodiments of the present invention will be described with reference to the accompanying drawings wherein like reference numerals refer to like elements.

First Embodiment

Figure 1B:
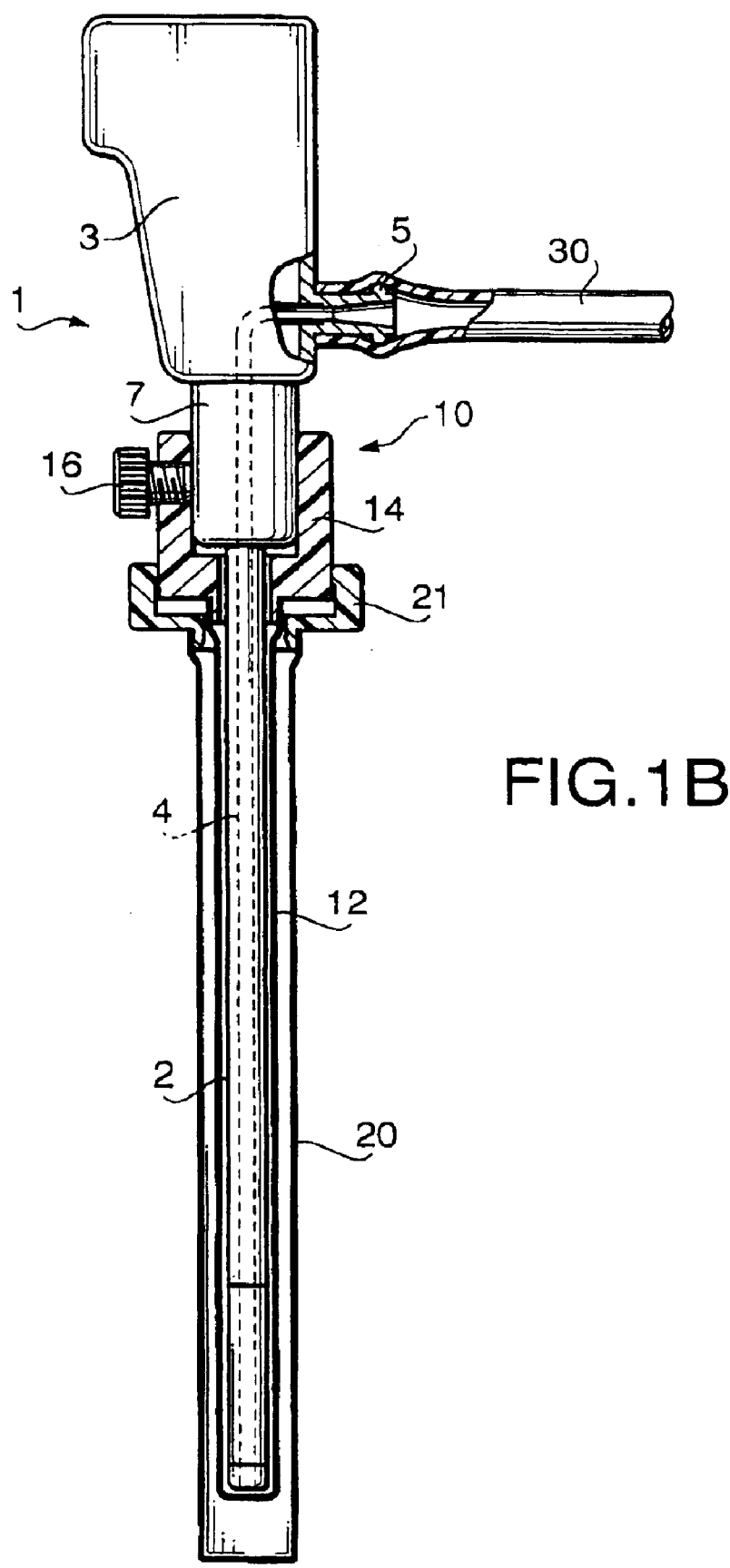

FIGS. 1A through 1C show an endoscope 1 with a detachable sheath 10 and a sheath cover 20 according to a first embodiment of the invention. In particular, FIG. 1A shows the endoscope 1 and the sheath 10 separately, and FIG. 1B the endoscope 1 covered with both the sheath 10 and the sheath cover 20, and FIG. 1C the endoscope 1 covered with the sheath 10 but the sheath cover 20 removed.

The endoscope 1 is provided with a flexible inserting tube 2 and an operation portion 3 connected to the proximal end of the inserting tube 2. The inserting tube side of the operation portion 3 is formed as an engaging portion 7 which engages with the proximal end of the sheath 10 when the inserting tube 2 is covered with the sheath 10 as will be described later. The engaging portion 7 is a cylindrical member having a substantially uniform outer diameter along its longitudinal direction.

The endoscope 1 is also provided with an air feeding tube 4 which extends throughout the inserting tube 2. The distal end of the air feeding tube 4 is connected to an opening 6 formed at the distal end of the inserting tube 2, and the proximal end thereof is connected to a nipple 5 provided to the back side of the operation portion 3, or the side opposite to the operator handling the operation portion 3.

The nipple 5 is adapted to be connected with a tube 30 of an air supplying device (not shown). When the tube 30 is connected to the nipple 5 and air is supplied thereto, the air flows through the air feeding tube 4 and flows out from the opening 6 at the distal end of the inserting tube 2.

The sheath 10 includes an elastic tubular member 12 and a cylindrical mounting member 14.

The elastic tubular member 12 has a thin cylindrical wall made of elastic and transparent material such as silicon rubber, soft polyvinyl, polyurethane or the like. The tubular member 12 is formed such that its inner diameter is slightly smaller than the outer diameter of the inserting tube 2 of the endoscope 1. Accordingly, when the sheath 10 covers the inserting tube 2, the elastic tubular member 12 comes in intimate contact with the outer circumferential surface of the inserting tube 2.

A proximal end 12a of the elastic tubular member 12 is opened while a distal end 12b thereof is closed in an airtight manner. Since the elastic tubular member 12 is made from transparent material, the closed distal end 12b thereof is also transparent and allows the observation of things therethrough.

It should be noted that elastic tubular member may be also formed such that only the distal end portion thereof is made from transparent material and the rest from opaque material such as natural rubber. Alternatively, the distal end 12b of the tubular member 12 may also be closed with a transparent cap like member made of styrol resin or the like.

The cylindrical mounting member 14 is fixed to the proximal end 12a of the elastic tubular member 12. The cylindrical mounting member 14 is made from a relatively hard material such as metal and plastic and has a proximal side portion 14a and a distal side portion 14b.

The proximal side portion 14a has an inner diameter large enough for receiving the engaging portion 7 of the endoscope 1 therein with a clearance therebetween. The distal side portion 14b is formed to have an inner diameter smaller than the outer diameter of the engaging portion 7 but still large enough for allowing the inserting tube 2 to pass therethrough with a gap therebetween.

The proximal side portion 14a is provided with a screw hole 14c that penetrates the circumferential wall thereof in a direction perpendicular to a center axis A of the mounting member 14. A screw 16 is screwed into the screw hole 14c, which has a knob 16a at the head thereof for being manually tightened and loosened.

The sheath cover 20 is a tubular member for surrounding the elastic tubular member 12 of the sheath 10 to prevent overinflation thereof. The sheath cover 20 is made of a material, e.g. plastic or the like, that has sufficient strength for resisting the inflating force of the elastic tubular member 12.

The distal end of the sheath cover 20 is closed while the proximal end thereof is opened to receive the elastic tubular member 12 therein. An elastic fitting member 21 is provided to the proximal end of the sheath cover 20 which is to be elastically deformed and thereby detachably fitted on the distal end of the mounting member 14.

The sheath cover 20 surrounds the tubular member 12 of the sheath 10 with a space left therebetween so that the tubular member 12 can inflate to a size enough for allowing the inserting tube 2 to be inserted, but not so large that it bursts.

The inserting tube 2 of the endoscope 1 is inserted into the sheath 10 to be covered therewith in the following manner.

First, the elastic tubular member 12 of the sheath 10 is inserted into the sheath cover 20 and the elastic fitting member 21 is fixed to the mounting member 14.

Next, the tube 30 of the air supplying device is connected to the nipple 5 of the endoscope 1. Air is supplied through the tube 30 into the nipple 5 and hence into the air feeding tube 4 so that air flows out from the opening 6 at the distal end of the inserting tube 2.

Next, the distal end of the inserting tube 2 is inserted through the cylindrical mounting member 14 and into the elastic tubular member 12.

Figure 2:
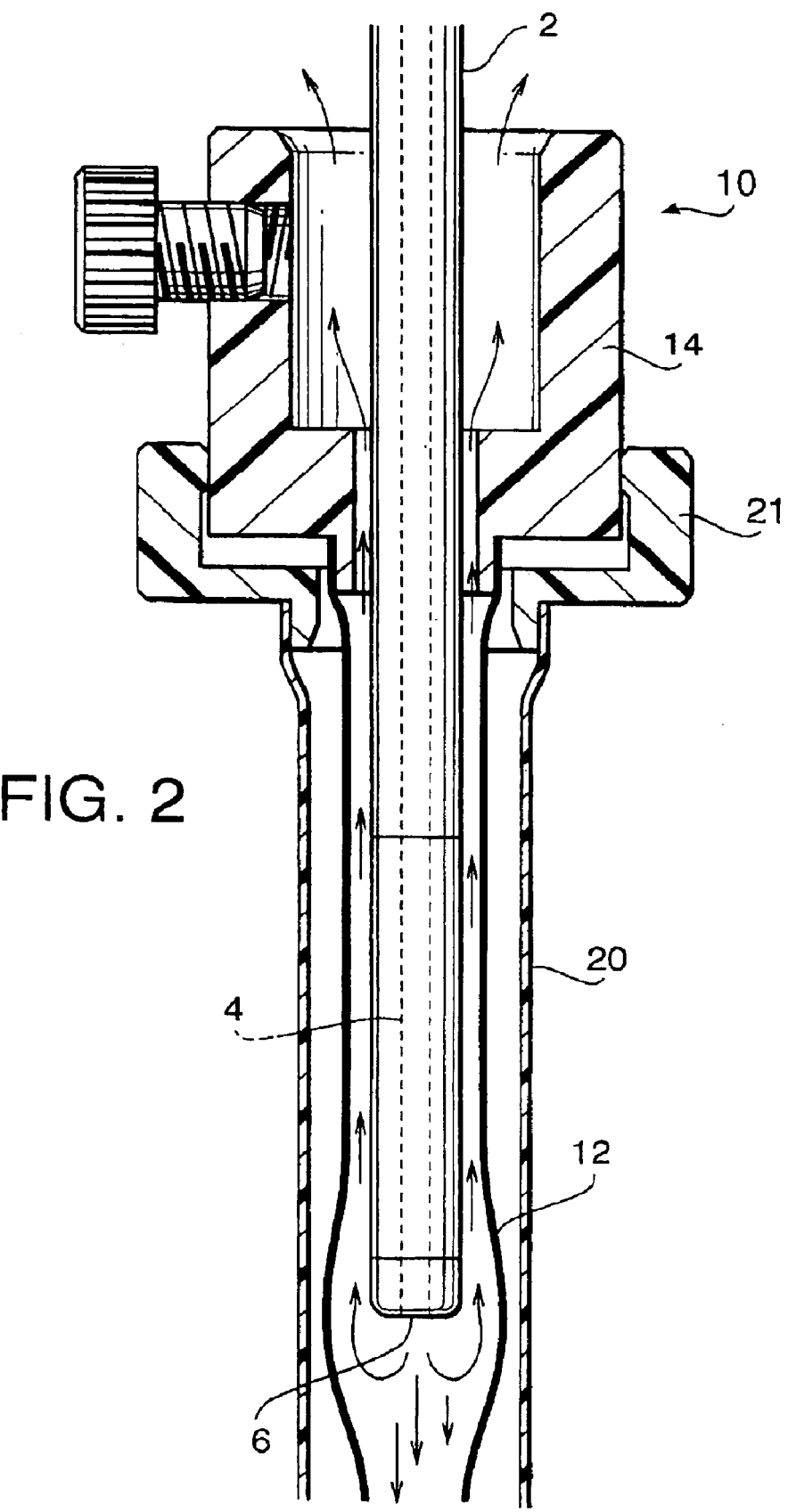

FIG. 2 schematically shows the inserting tube 2 that is partially inserted into the elastic tubular member 12 of the sheath 10. As shown in FIG. 2, the pressure of the air flowing out from the opening 6 of the inserting tube 2 inflates the elastic tubular member 12, in particular, near the distal end of the inserting tube 2. Accordingly, the inserting tube 2 can be smoothly inserted into the elastic tubular member 12. A part of the air flows between the inserting tube 2 and the elastic tubular member 12 towards the mounting member 21 and thereby prevents the elastic tubular member 12 from adhering onto the inserting tube 2. The air further flows through the gap formed between the inserting tube 2 and the mounting member 14 and out to the exterior. Thus, the air pressure within the sheath 10 is kept from becoming extremely high.

The inserting tube is inserted into the sheath 12 until the cylindrical mounting member 14 receives the engaging portion 7 therein. Then, the air feeding through the air feeding tube 4 is stopped so that the inflated tubular member 12 contracts and comes into intimate contact with the inserting tube 2 (see FIG. 1B).

Next, the screw 16 is manually-tightened to fix the mounting member 14 to the engaging portion 7. Then, the elastic fitting member 21 is taken off from the mounting member 14 and then the sheath cover 20 is removed to allow endoscopic inspection with the sheathed endoscope 1 (see FIG. 1C).

After the endoscopic inspection, the sheath 10 is removed from the inserting tube 2 by performing the above described procedure in the inverse order and discarded together with the sheath cover 20.

It should be noted that the sheath 10 according to the first embodiment has a simple arrangement that can be produced at low cost since the air feeding tube 4 is provided to the endoscope 1 and the sheath 10 itself does not have any conduit for air feeding. Thus, the sheath 10 does not cause significant increase in the cost of endoscopic inspection even if it is exchanged and discarded for each inspection.

Second Embodiment

Figure 3A:
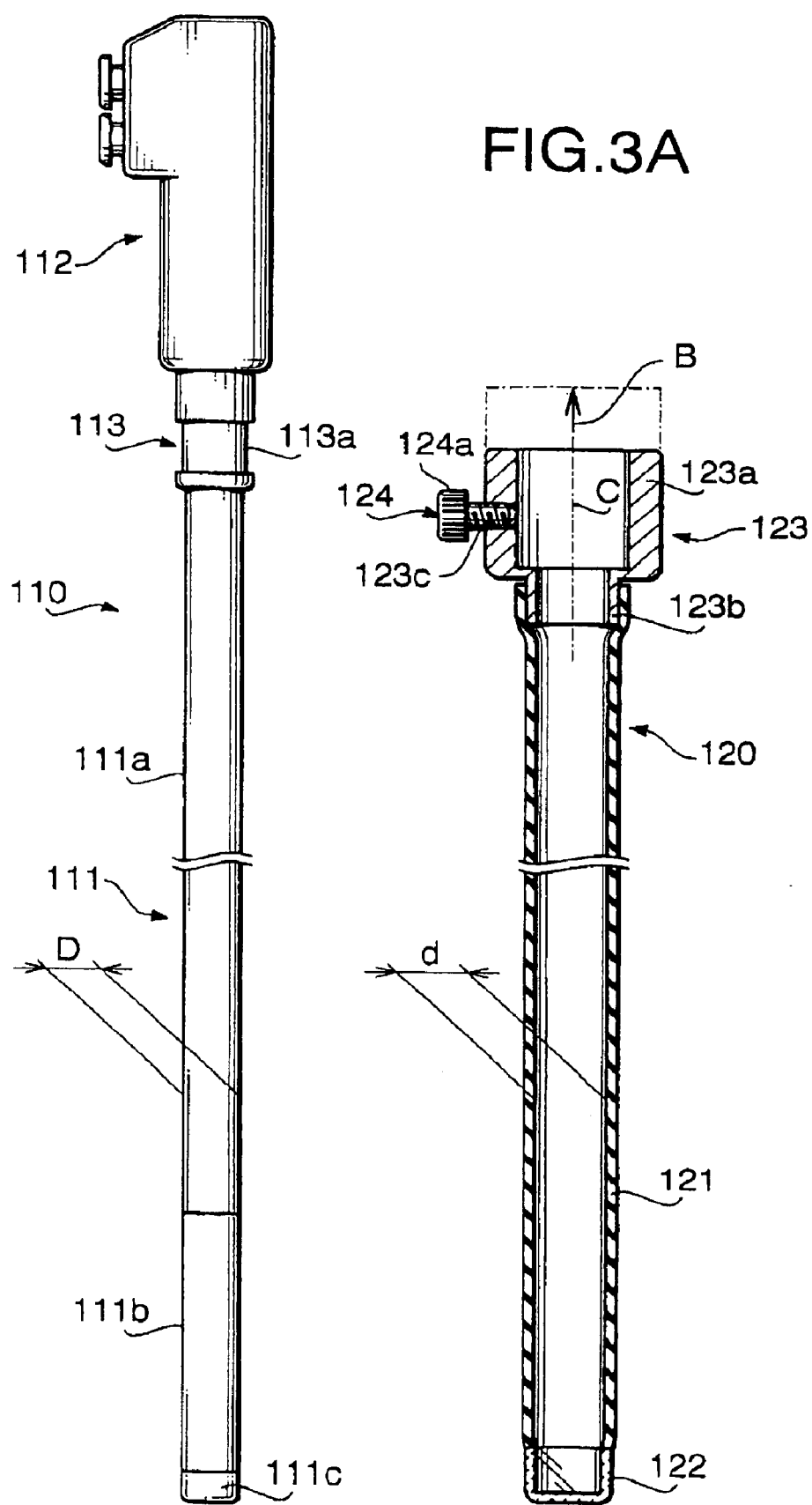
FIGS. 3A and 3B show an endoscope with a detachable sheath according to a second embodiment of the invention.
Figure 3B:
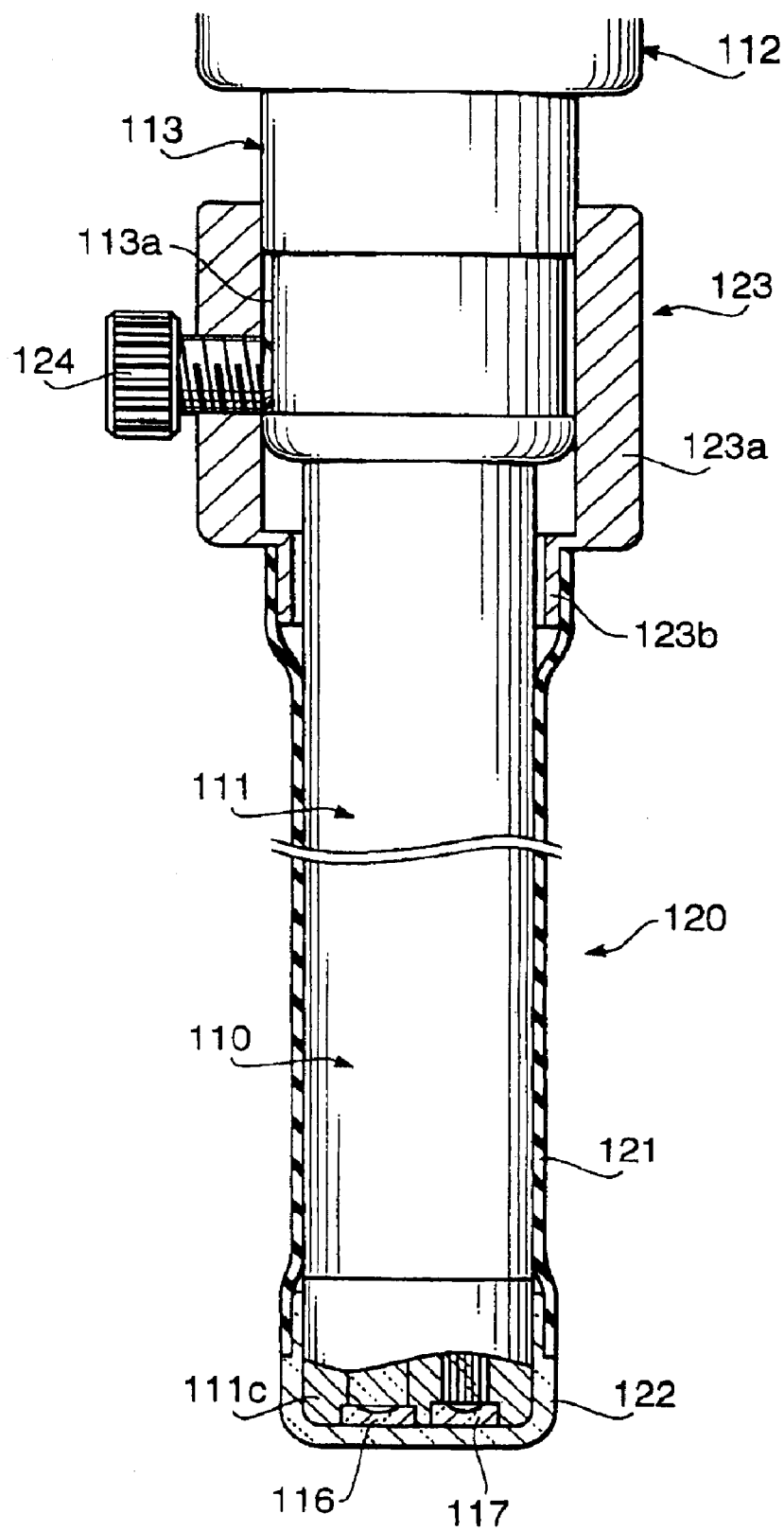

FIGS. 3A and 3B show an endoscope 110 with a detachable sheath 120 according to a second embodiment of the invention. In particular, FIG. 3A shows the endoscope 110 and the sheath 120 separately, and FIG. 3B shows the endoscope 110 covered with the sheath 120.

The endoscope 110 includes an inserting tube 111 that is to be inserted into a human body, and an operation portion 112 connected to the proximal end of the inserting tube 112. The inserting tube 111 includes a flexible tube 111a having a bending portion 111b at the distal end side thereof. The bending portion 111b is part of the inserting tube 111 of which bending can be remotely controlled from the operation portion 112. A tip body 111c, which is provided with an observation window 116 and an illumination window 117, is mounted to the tip end of the bending portion 111b.

A sheath engaging portion 113 is formed at the lower end of the operation portion 112, or at the portion the inserting tube 111 is connected. The sheath engaging portion 113 is a portion at which a cylindrical mounting member 123 of the sheath 120, which will be described later, is to be fixed when the inserting tube 111 is covered with the sheath 120. The sheath engaging portion 113 is a cylindrical member having a circumferential groove, or an engaging groove 113a, on the outer circumferential surface thereof.

The sheath 120 includes an elastic tubular member 121 which is fixed to a cap member 122 at the distal end thereof and connected to the cylindrical mounting member 123 at the proximal end thereof.

The tubular member 121 is made from elastic material such as silicon rubber, natural rubber, polyurethane or the like and have a inner diameter d larger than the outer diameter D of the inserting tube 111, i.e. d>D. If the outer diameter D of the inserting tube 111 varies along the longitudinal direction thereof, the tubular member 121 is formed such that the inner diameter d thereof is larger than the largest outer diameter D of the inserting tube 111.

It should be noted that the tubular member 121, which is made from elastic material, is able to stretch in a main axis direction B thereof, as shown in FIG. 3A, to reduce the inner diameter d until it becomes smaller than the outer diameter D of the inserting tube 111.

The cap member 122 is made from transparent plastic and shaped in a form that allows the tip body 111c of the inserting tube 111 to be smoothly received therein. The cap member 122 is fixed to the distal end of the tubular member 121 in an airtight manner. Thus, the interior of the tubular member 121 is in communication with the exterior only at the proximal end thereof.

The mounting member 123 is a cylindrical member that is to be detachably fixed to the sheath engaging portion 113 of the endoscope 110. The mounting member 123 includes a proximal side portion 123a and a distal side portion 123b. The proximal side portion 123a has an inner diameter large enough for receiving the sheath engaging portion 113 of the endoscope 110 therein, while the distal side portion 123b has a smaller inner diameter that allows the inserting tube 111 passing therethrough but not the sheath engaging portion 113.

A screw hole 123c is formed to the proximal side portion 123a so as to penetrate the wall of the mounting member 123 in a direction substantially perpendicular to the center axis C thereof. A screw 124 is screwed into the screw hole 123c, the screw having a knob 124a at the head thereof for manually screwing it in and out. The mounting member 123 can be fixed to the sheath engaging portion 113, as shown in FIG. 3B, by screwing in the screw 124 until the tip thereof is located within the engaging groove 113a.

As shown in FIG. 3A, the elastic tubular member 121 of the sheath 120 is formed shorter than the inserting tube 111 of the endoscope 110. Therefore, the mounting member 123 cannot be engaged with the sheath engaging portion 113 if the inserting tube 111 is only inserted into the sheath 120 but the mounting member 123 should be pulled towards the sheath engaging portion 113 which causes the sheath 120 to be stretched.

The inserting tube 111 of the endoscope 110 is inserted into the sheath 120 to be covered therewith in the following manner.

First, the inserting tube 111 is inserted into the sheath 120 until the tip body 111c abuts against the cap member 122 fixed at the distal end of the tubular member 121. It should be noted that the inserting tube 111 can be smoothly inserted into the sheath 120 since the inner diameter d of the tubular member 121 thereof is larger than the outer diameter D of the inserting tube 111.

Next, the mounting member 123 is pulled towards the sheath engaging portion 113 until the screw 124 is located at the engaging groove 113a. As the mounting member is pulled, the elastic tubular member 121 of the sheath 120 is stretched and the inner diameter d thereof is reduced. As a result, the elastic tubular member 121 comes in intimate contact with the outer circumference surface of the inserting tube 111.

Next the screw 124 is manually screwed in by operating the knob until the tip of the screw 124 is placed within the engaging groove 113a of the sheath engaging portion 113. Thus, the mounting member 123 is fixed to the sheath engaging portion 113 and the elastic tubular member 121 is kept in the stretched condition.

It should be noted that if the engaging groove 113a is formed relatively wide, the stretched amount of the elastic tubular member 121, and in turn the reduction in diameter thereof, can be adjusted by varying the location at which the screw 124 is tighten against the engaging groove 113a in the width direction thereof (up and down direction in FIG. 3A).

It should be also noted that the engaging groove 113a is formed deep enough so that the tip of the screw 124 remains in the engaging groove 113a even if the screw 124 becomes loose and thereby keeps the mounting member 123 from coming off from sheath engaging portion 113.

The sheath 120 is removed from the endoscope 110 by performing the above described procedure in the inverse order. That is, the screw 124 is loosened to allow the mounting member 123 to be taken off from the sheath engaging portion 113 and move gradually towards the distal end of the inserting tube 111. As a result, the inner diameter d of the elastic tubular member 121 recovers to the initial size and allows the inserting tube 111 to be pulled out.

It should be noted that the sheath 120 is not inflated by feeding air thereinto to put on or remove it from the inserting tube 111. Accordingly, the endoscope 110 and the sheath 120 according to the second embodiment of the invention do not require any air feeding device.

It should be also noted that the sheath 120 can be easily removed from the endoscope even if pin holes are formed thereto during endoscopic inspection, in which case it is difficult to inflate the sheath.

Figure 4:
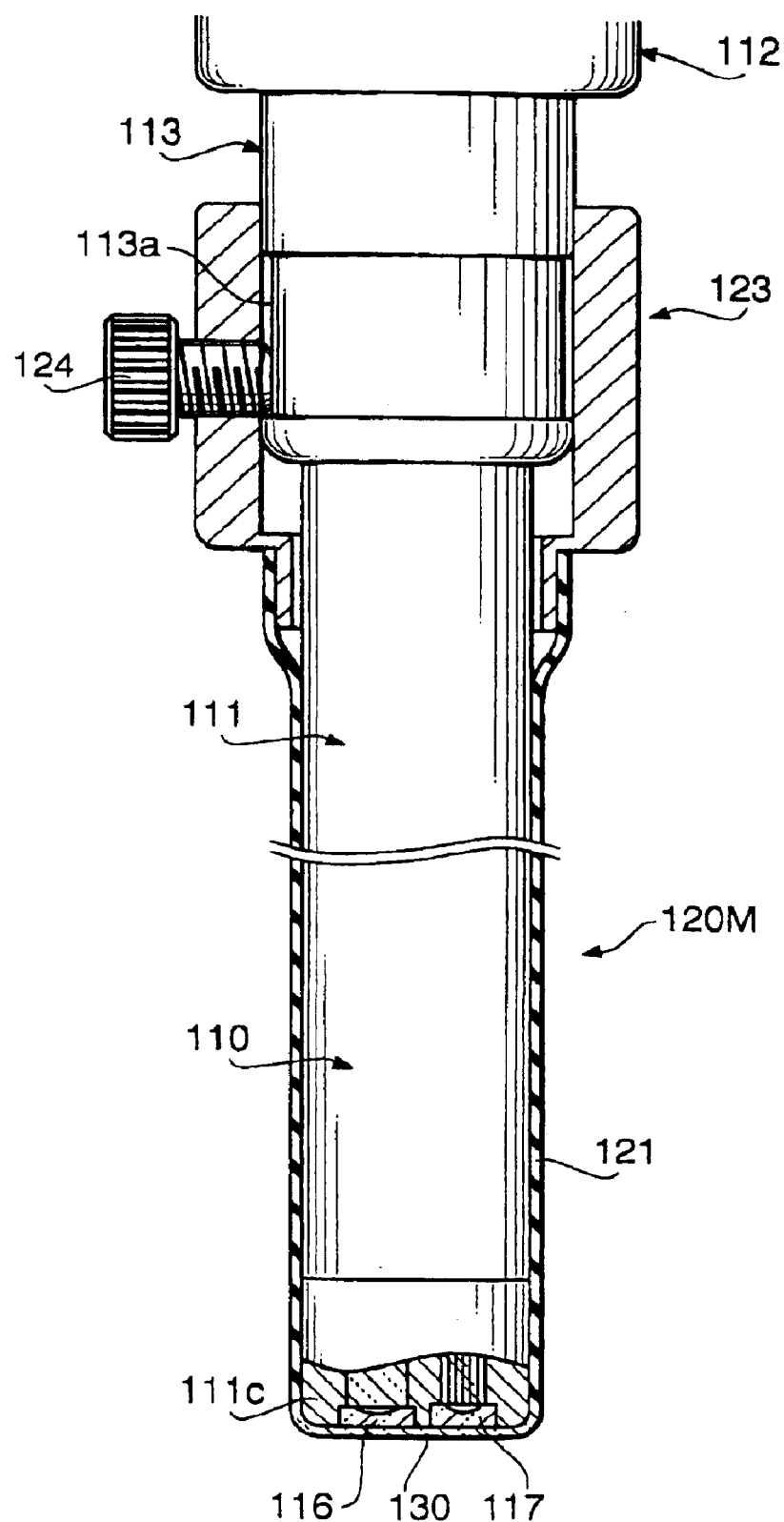
FIG. 4 shows a modification of the sheath shown in FIG. 3A.

FIG. 4 shows the inserting tube 111 covered with a sheath 120M which is a modification of the sheath 120 shown in FIG. 3A. The sheath 120M shown in FIG. 4 differs from that shown in FIG. 3A in that the distal end of the tubular member 121 is closed in an air tight manner with elastic and transparent material 130, such as silicon rubber, soft polyvinyl chloride and polyurethane, instead of being closed with the cap member 122. The sheath 120M arranged as above fits well on the front surface of the tip body 111c of the endoscope 110 even when it has projections and/or depressions thereon about the observation window 116 or the like.

Figure 5A:
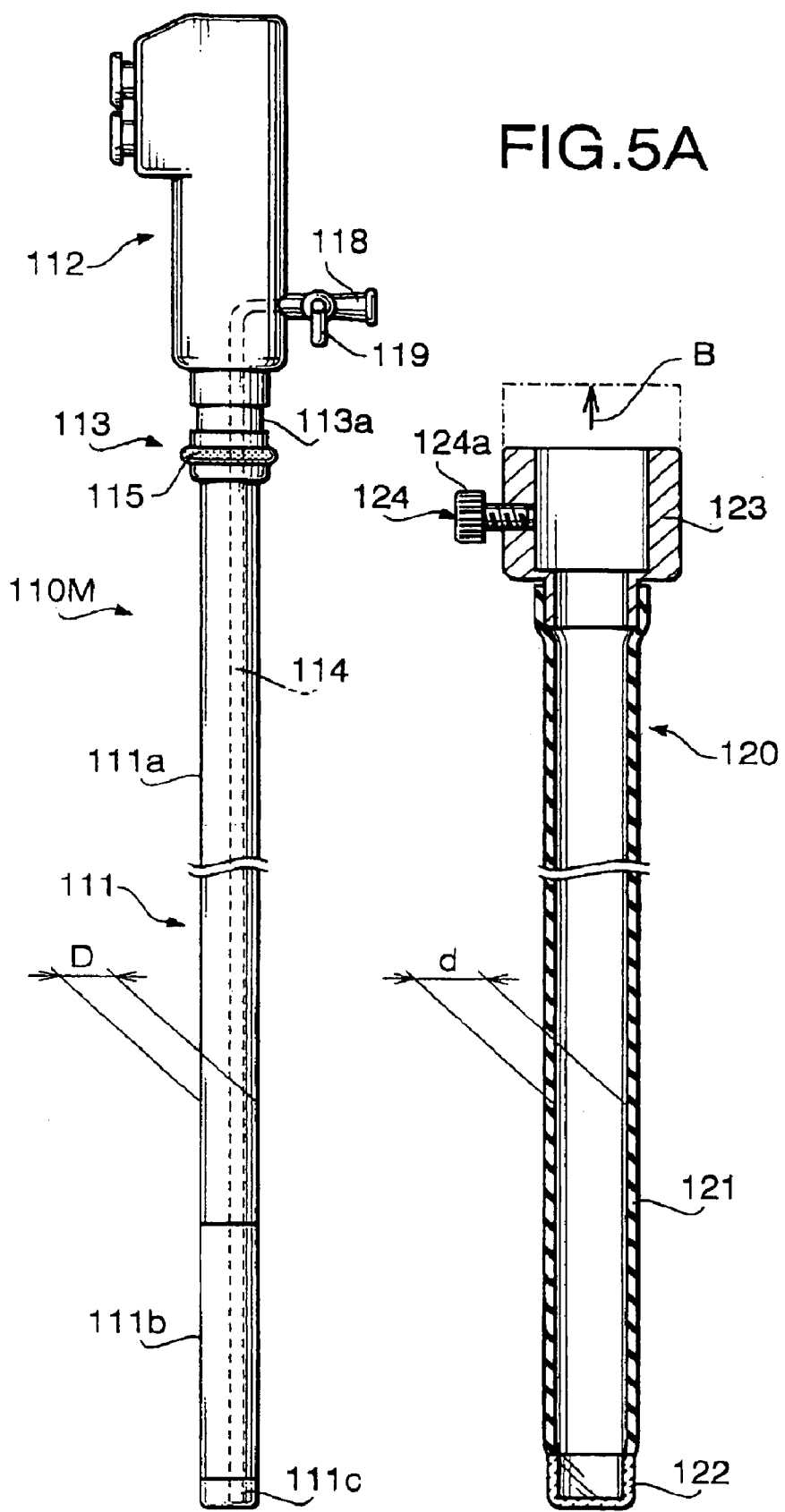
FIGS. 5A and 5B show the sheath of FIG. 3A together with an endoscope which is a modification of the endoscope shown in FIG. 3A.
Figures 5B, 6:
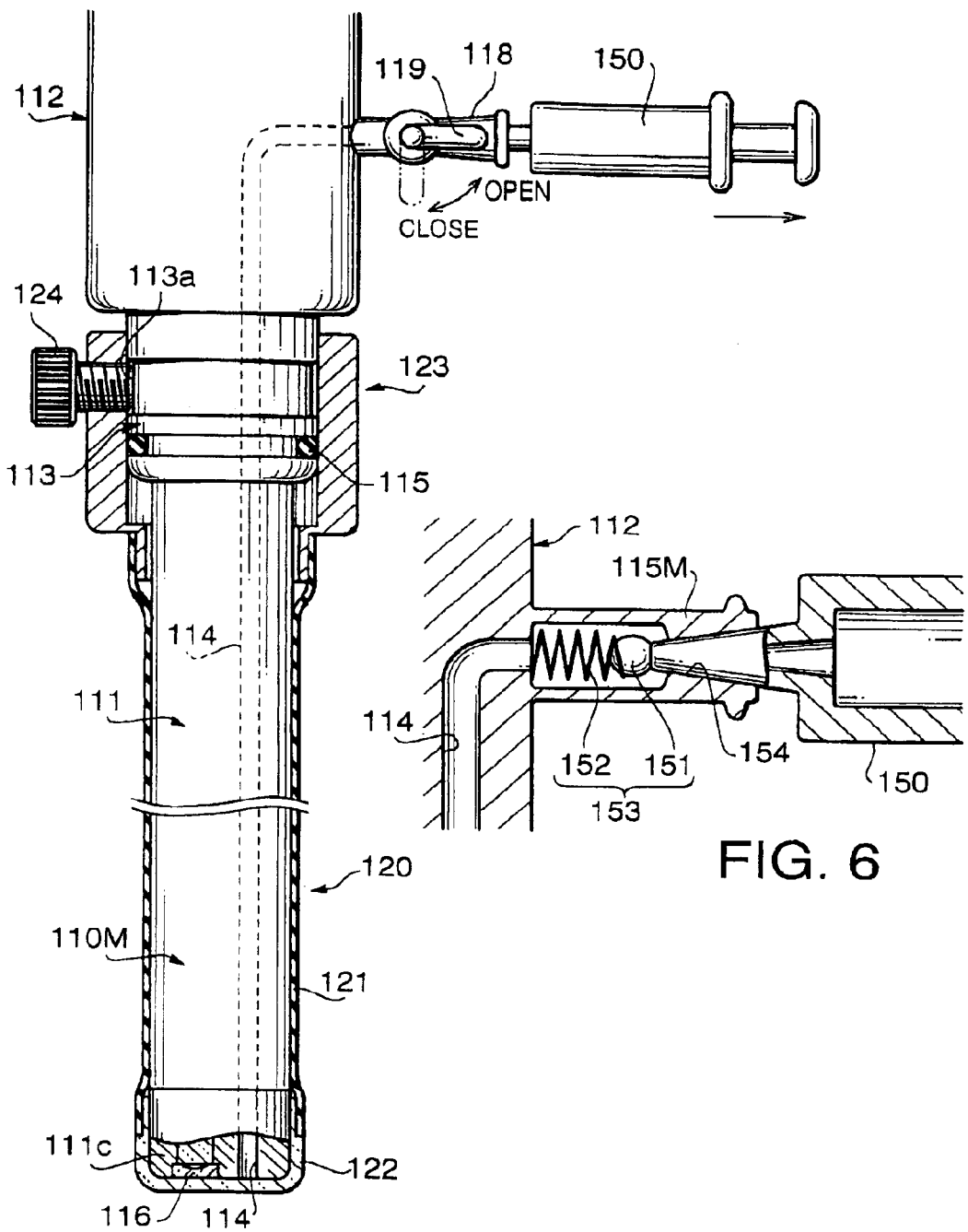
FIG. 6 shows a sectional view of an example of a nipple of the endoscope shown in FIG. 5A.

FIGS. 5A and 5B show the-sheath 120 of FIG. 3A together with an endoscope 110M which is a modification of the endoscope 110 shown in FIG. 3A. In particular, FIG. 5A shows the endoscope 110M and the sheath 120 separately, and FIG. 5B shows the endoscope 110M covered with the sheath 120.

The endoscope 110M shown in FIGS. 5A and 5B is arranged essentially the same as the endoscope 110 shown in FIG. 3A except that it is provided with an O-ring 115 and an air suction tube 114.

The O-ring 115 is provided on the outer circumferential surface of the sheath engaging portion 113 between the engaging groove 113a and the end at the inserting tube side thereof.

The air suction tube 114 is provided to the endoscope 110M such that it extends within the inserting tube throughout the entire length thereof. One end of the air suction tube 114 opens at the end of the tip body 111c while the other end is connected to a nipple 118 provided to the back side of the operation portion 112. The nipple 118 is provided with a manually operatable cock 119 for open/close the nipple 118.

The inserting tube 111 of the endoscope 110M shown in FIG. 5B is covered with the sheath 120 in the following manner.

First, the cock 119 of the nipple 118 is turned to its open position and then the inserting tube 111 is inserted into the sheath 120. Next, the mounting member 123 is pulled up until the sheath engaging portion 113 is received therein. Then, the screw 124 is tightened to fix the mounting member 123 to the sheath engaging portion 113.

In this state, the elastic tubular member 121 of the sheath 120 is reduced in its diameter and hence the tubular member 121 adheres on the outer surface of the inserting tube 111. The O-ring 115 is located between the mounting member 123 and the sheath engaging portion 113, as shown in FIG. 5B, and seals the space within the sheath 120.

Next, a suction device 150 such as a syringe 150 is connected to the nipple 118 as shown in FIG. 5B. The syringe 150 is operated to suck air through the air suction tube 114. As a result, the air remaining between the sheath 120 and the inserting tube 111 is sucked out and hence the tubular member 121 of the sheath 120 adheres strongly on the entire outer surface of the inserting tube 111. Thus, the tubular member 121 does not float from the outer surface of the inserting tube 111 and hence is kept from becoming wrinkled, even if the endoscope 110 is bent. After the air is sucked out, the cock 119 of the nipple is moved to the closed position to seal the space within the sheath 120.

When the sheath 120 is to be removed, the cock 119 is first operated to the open position so that the space inside the sheath 120 comes in communication with the exterior through the air sucking tube 114. Then, the sheath 120 is removed in the same manner as it is removed from the endoscope 110 shown in FIG. 3B.

FIG. 6 shows a sectional view of a nipple 115M which is a modification of the nipple 118 shown in FIG. 5A. The nipple 115M includes an automatic valve 153 instead of the cock 119.

The automatic valve 153 includes a sphere 151 and a spring 152 that biases the sphere 151 against an opening 154 to which the syringe 150 is to be connected. When the syringe 150 is connected to the nipple 115M the sphere 151 is pushed away from the opening 154 by the tip of the syringe 150 and thereby the nipple 115M is opened. When the syringe 150 is removed from the nipple 115M, the spring 152 biases the sphere 151 back to close the opening, or close the nipple 115M. Thus, if the syringe is removed from the nipple 151M after the air within the sheath 120 is sucked, the nipple 151M is automatically closed and seals the space within the sheath 120.

It should be noted that, although the embodiments of the invention are described separately, any suitable combination among the above-described embodiments and variations of the same should also be the subject of the present invention.

The present disclosure relates to the subject matters contained in Japanese Patent Applications No. P2001-327085 and NO. P2001-327086, both filed on Oct. 25, 2001, and No. P2001-332345, filed on Oct. 30, 2001, which are expressly incorporated herein by reference in their entireties.

What is claimed is:

1. A combination of an endoscope and a sheath for covering an inserting tube of said endoscope,
   wherein said sheath includes an elastic tubular member, said elastic tubular member having an open proximal end and a closed distal end, and
   said endoscope includes an air feeding tube for feeding air from a distal end of said inserting tube to inflate said tubular member when said inserting tube is inserted into said tubular member to be covered therewith.

2. The combination according to claim 1, wherein said tubular member has an inner diameter smaller than an outer diameter of said inserting tube.

3. The combination according to claim 1, wherein said air feeding tube is arranged to be connectable with an external air supplying device at an operation portion of said endoscope.

4. The combination according to claim 3,
   wherein a nipple is provided to said operation portion, said nipple being connectable with an air supply tube of the external air supplying device, and
   wherein said air feeding tube is in communication with said nipple.

5. The combination according to claim 1, wherein said open proximal end of said tubular member is connected to a cylindrical mounting member, said cylindrical mounting member being fixable to said endoscope to keep said tubular member from coming off from said inserting tube, at least a part of said mounting member being formed so as to allow said inserting tube to pass therethrough with a gap therebetween for discharging air fed into said tubular member through said air feeding tube.

6. The combination according to claim 1, wherein a distal end of said tubular member is closed in an airtight manner with a transparent cap member formed to receive a distal end of said inserting tube therein.

7. The combination according to claim 1, wherein said tubular member comprises an elastic transparent member, and wherein a distal end of said tubular member is closed in an airtight manner.

\* \* \* \* \*